United States Patent [19]
Burdea et al.

[11] Patent Number: 5,429,140
[45] Date of Patent: Jul. 4, 1995

[54] INTEGRATED VIRTUAL REALITY REHABILITATION SYSTEM

[75] Inventors: Grigore C. Burdea, 2 Holly Ct., Highland Park, N.J. 08904; Noshir A. Langrana, Robbinsville, N.J.

[73] Assignees: Greenleaf Medical Systems, Inc., Palo Alto, Calif.; Grigore C. Burdea, Highland Park; Noshir Langrana, Robbinsville, both of N.J.

[21] Appl. No.: 72,979

[22] Filed: Jun. 4, 1993

[51] Int. Cl.⁶ .............................................. A61B 5/103
[52] U.S. Cl. ..................................................... 128/774
[58] Field of Search ................ 128/774, 782, 779, 781; 33/511, 512

[56] References Cited

U.S. PATENT DOCUMENTS

| | | | |
|---|---|---|---|
| 4,414,984 | 11/1983 | Zarudiansky | 128/774 |
| 4,922,925 | 5/1990 | Crandall et al. | 128/782 |
| 4,972,074 | 11/1990 | Wright | 250/227.11 |
| 4,986,280 | 1/1991 | Marcus et al. | 128/774 |
| 5,005,140 | 4/1991 | Havriluk | 364/550 |
| 5,082,001 | 1/1992 | Vannier et al. | 128/774 |
| 5,086,785 | 2/1992 | Gentile et al. | 128/782 |
| 5,143,505 | 9/1992 | Burdea et al. | 414/5 |
| 5,163,228 | 11/1992 | Edwards et al. | 33/1 N |
| 5,165,897 | 11/1992 | Johnson | 434/113 |
| 5,184,009 | 2/1993 | Wright et al. | 250/227.11 |
| 5,184,319 | 2/1993 | Kramer | 364/806 |
| 5,191,895 | 3/1993 | Koltringer | 128/736 |

OTHER PUBLICATIONS

Engineering News, Dec. 1991, No. 8.
Journal of Rehabilitation Research and Development, vol. 27, No. 4, 1980, pp. 411-424.

*Primary Examiner*—Max Hindenburg
*Attorney, Agent, or Firm*—Mathews, Woodbridge & Collins

[57] ABSTRACT

A rehabilitation system employs a force feedback system, such as a force feedback glove, to simulate virtual deformable objects. Prior to rehabilitation, the patient places his or her hand in a sensing glove which measures the force exertable by the patient's digits. Information from the sensing glove is received by an interface and transmitted to a computer where the information can be used to diagnose the patient's manual capability. The computer generates rehabilitation control signals for a force feedback glove. The patient places his or her hand in the force feedback glove and attempts to bring the digits together as though grasping the virtual object. The force feedback glove resists the squeezing movement of the digits in a manner that simulates the tactile feel of the virtual object. The force exerted by the fingers of the patient is fed back to the computer control system where it can be recorded and/or used to modify future rehabilitation control signals. The basic concept of rehabilitation in virtual environment with force feedback can also be applied to other appendages of the human body including arms, legs, neck, knees, elbows and other articulated joints.

19 Claims, 7 Drawing Sheets

PATIENT HAND WITH REAL OBJECT

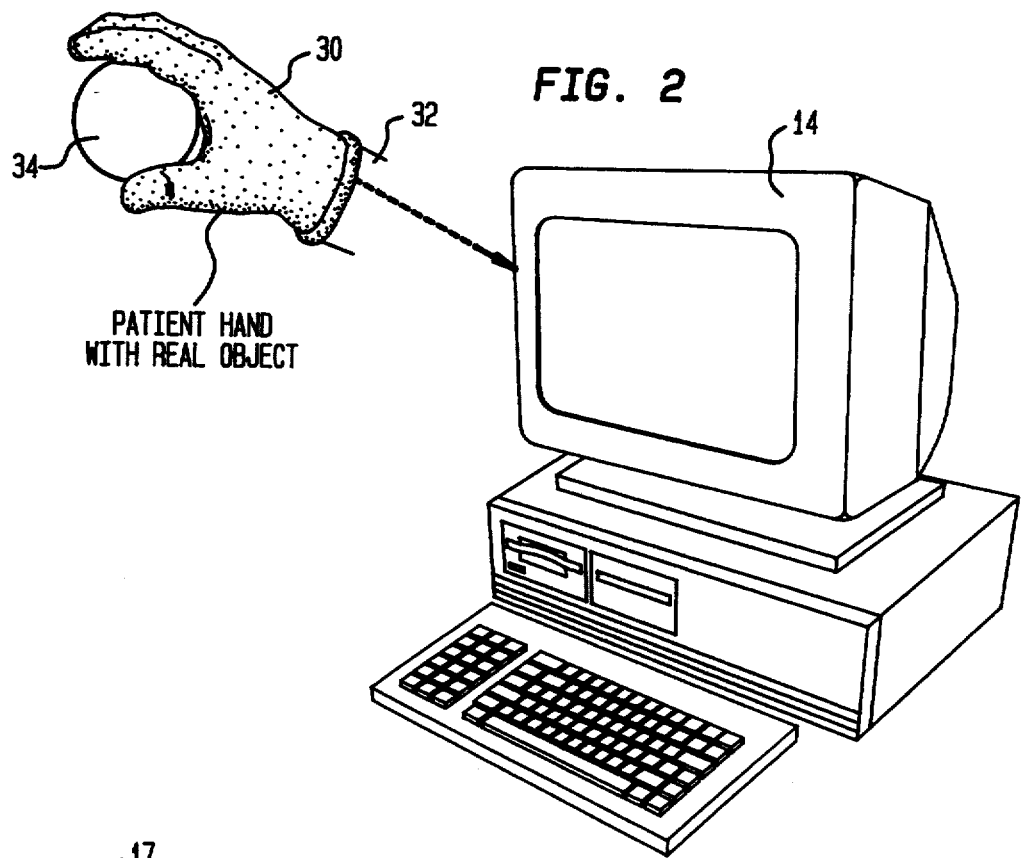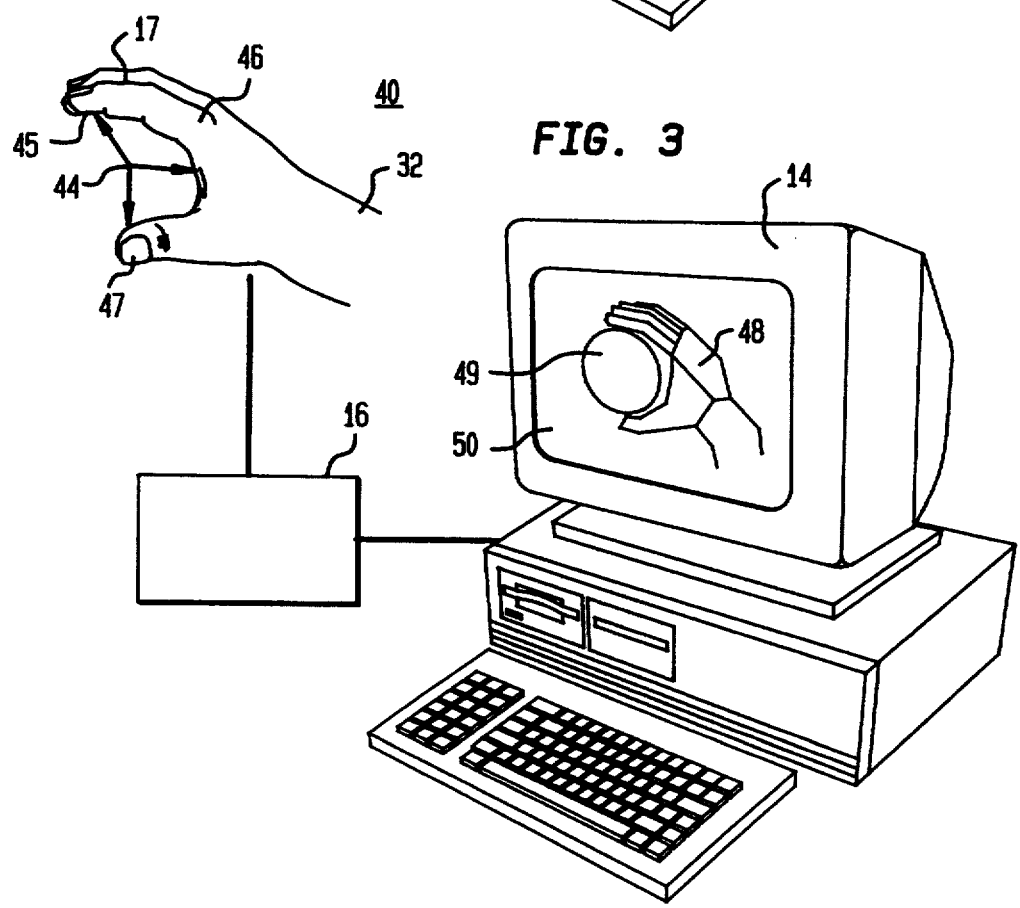

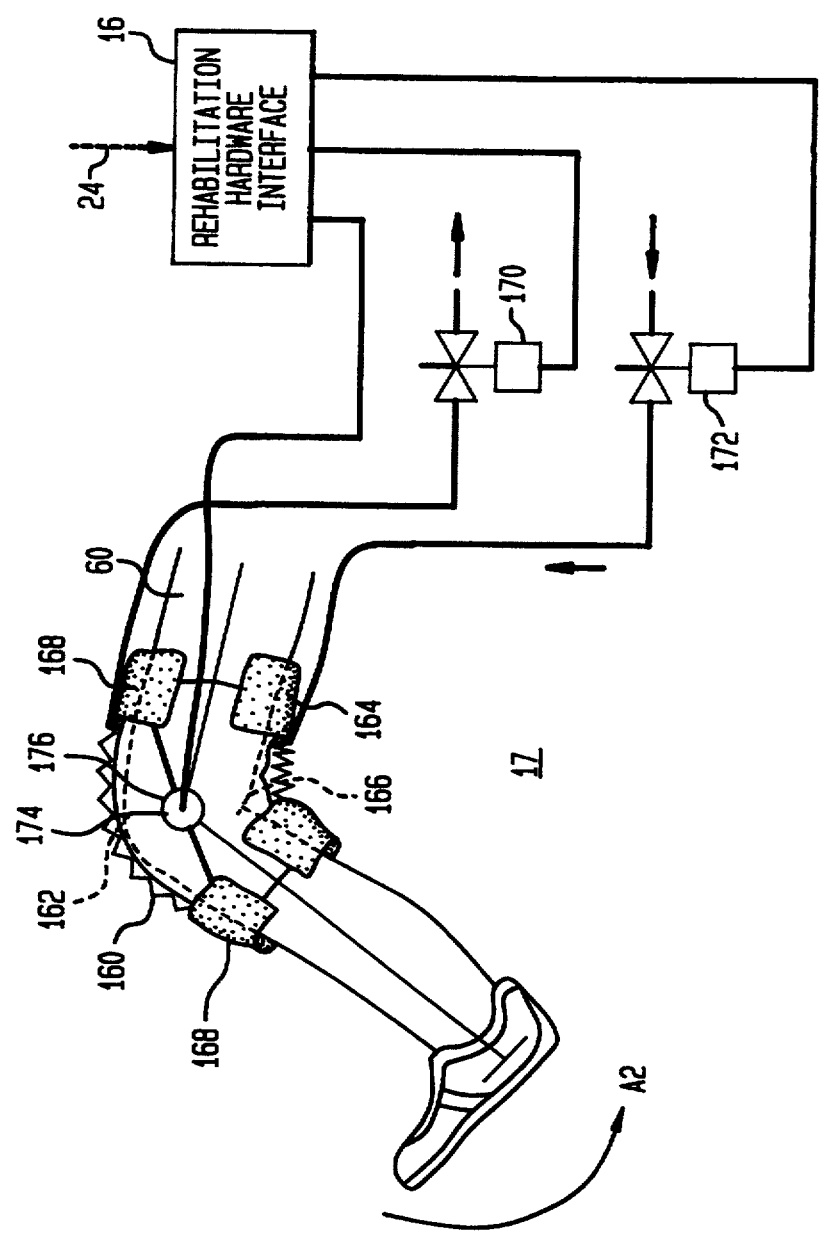

INTEGRATED VIRTUAL REALITY REHABILITATION SYSTEM

BACKGROUND OF THE INVENTION

1. Field of the Invention

The invention relates to a rehabilitation system and method in which the appendage of a human being is first diagnosed by a data gathering mechanism and then rehabilitated through the use of virtual reality and a force feedback device such as a force feedback glove.

2. Description of the Related Art

It is known that a computer based evaluation system can be used for measuring various physical parameters of a patient's anatomy. U.S. Pat. No. 4,922,925 describes an upper extremity evaluation system including a computer directly connected to a three dimensional position locator. A pointer or wand is brought into contact with the body part for measuring the angles of maximum flexion and extension of distal segments at the joints in the fingers of the hand. Data from the position locator is entered and stored in the computer. Range of motion is calculated from the data stored in the computer. However, the drawback of this device is that the device does not provide instruction and feedback to a patient during rehabilitation therapy.

Other patents directed to computer monitoring and measurement of a patient include: U.S. Pat. No. 5,005,140 to Havriluk entitled "METHOD AND APPARATUS FOR MONITORING HYDRODYNAMIC THERAPY AND EXERCISE"; U.S. Pat. No. 5,191,895 to Koltringer entitled "METHOD AND APPARATUS FOR THE DIAGNOSIS OF POLYNEUROPATHY SYNDROMES"; and U.S. Pat. No. 4,922,905 to Crandall, et al. entitled "COMPUTER BASED UPPER EXTREMITY EVALUATION SYSTEM". Systems for clinical hand measurements are also manufactured by Exos,Inc., 8 Blanchard Road, Burlington, Mass. 01823 as the Exos Clinical HandMaster System TM and Greenleaf Medical, 2248 Park Blvd., Palo Alto, Calif. 94306 as Compact EVAL. The above patents provided limited data measurements related to human appendage positioning.

Interactive devices have been described to provide more accurate data measurements of the positioning of a human appendage in order to interface and control robotic functions. An example of an interactive device is the DataGlove TM developed by VPL Research, Inc., 950 Tower Lane, 14th Floor, Foster City, Calif. 94404. DataGlove TM translates hand and finger movements into electrical signals to control a remote robot. Sensor gloves such as the DataGlove TM typically include fiber optic sensors that are located on the back of the glove such that movement of the fingers is sensed by the fiber optic sensors and transmitted though fiber optic bundle of cables to a glove interface.

U.S. Pat. No. 5,184,009 relates to a real time optical attenuation measurement system for improving response time of a sensing glove. The system obtains signals proportional to movement of a body part to which it is attached. A light source transmits light into a conduit and the emitted light is detected at the other end of the conduit. The relative displacement of the fiber optic cable to the light source produces a signal which is converted into an electrical signal. This system is used on an operator's hand to detect movement of the hand and fingers for controlling a robotic hand which mimics the operator's hand movements.

The use of a data glove for hand evaluation was described by Wise, et al., in the Journal of Rehabilitation Research and Development, Volume 27, November, 1990, pp 411–424. Measurements were taken after a person squeezed a plaster mold for determine the force asserted by the person on the mold. It was determined that a Data Glove TM could be used as a semi-automated goniometric measuring device for hand range of motion (ROM) evaluation.

Other examples of sensing and measuring systems for the fingers include U.S. Pat. No. 4,986,280 to Marcus, et al. which describe a system for measuring the angular orientation of a human joint or angular finger movement; and, U.S. Pat. Nos. 4,972,024 and 5,184,009 which relate to a control system for sensing human finger movements. Sensing gloves and open loop measuring devices have the disadvantage that they lack the ability to bring force feedback to the operator's hand.

U.S. Pat. No. 5,143,505 ('505 patent), issued to G. Burdea, one of the inventors of this disclosure, describes an actuator system for providing force feedback to a dextrous master glove. An actuator for each digit receives input from sensors mounted on the glove. The actuator is a pneumatic cylinder for providing pressure feedback to the hand. A sphere joint permits rotation of the joints in a cone of about 60°. The system can be used in a virtual reality environment to provide artificial force feedback in response to a pseudo environment generated by a graphics workstation and host computer. In the virtual reality environment the force feedback system interacts with a host computer. The host computer provides input to a graphics workstation which on appropriate instructions, controls a pseudo robot slave hand or a module of a human hand and pseudo virtual objects. In response to the virtual reality environment, the feedback glove applies pressure to digits. The concept of employing pneumatic cylinders, such as are described in the '391 patent, to convey force information to the patient for diagnostic and rehabilitation of hand and wrist after surgery has been described in an article in the "Engineering News" (UK) dated December 1991.

U.S. Pat. No. 5,184,319 describes a non-machine interface for measuring body part positions and providing force and texture feedback to a user. A glove is capable of sensing digit and hand positions and exerting varied forces to each digit. The interface can be used with virtual or physical objects. This patent teaches that the force and texture feedback system can be used for telemanipulation, interactive 3-D graphics and Computer Aided Design (CAD).

Of general relevance are U.S. Pat. Nos. 4,414,984 to Zarudiansky; 5,086,785 to Gentile, et al.; 5,163,228 to Edwards, et al.; and, 5,165,897 to Johnson.

The foregoing examples illustrate prior art attempts for either measuring the position and force of the fingers or providing force feedback to the fingers. However, the inventors are unaware of any practical system which has yet been devised for providing a unified computerized diagnostic and rehabilitation system for a patient using data gathering and force feedback in virtual environment.

SUMMARY OF THE INVENTION

Briefly described, the invention comprises a system and method for rehabilitating human appendages. The invention can be used, for example, to rehabilitate arms, legs, elbows, shoulders, the neck, and other joints, but preferably is used to rehabilitate the hand. Initially, the patient places his or her hand in a data glove, or similar force measuring and position indicating instrument, to detect the position and force exertable by the digits of the affected hand. The output from the sensing glove is connected to an interface and fed to a workstation or similar computer. The computer analyzes the grasping force detected by the sensing glove and provides diagnostic information based upon those measurements and other statistics. The diagnostic information can be employed along with other rehabilitation information to produce rehabilitation control signals for a force feedback rehabilitation glove.

A typical force feedback glove includes a plurality of pneumatic cylinders which exert a force on one or more of the digits of the hand and a means for measuring the position and force exerted by the fingers in response thereto. According to the preferred embodiment, the force feedback glove is instructed to simulate a virtual reality object such as a deformable sphere. As the patient squeezes the imaginary sphere, the force exerted by the digits is detected, stored and analyzed in the computer. The feedback information can be used to dictate the number of repetitions of the squeeze, size and hardness of the virtual object, etc., to optimize the rehabilitation program for the specific patient. Other virtual reality deformable objects such as cylinders, squares, etc. can also be used. Interactive sound may be added to further motivate the patient. These and other features of the present invention may be more fully understood by reference to the following drawings.

BRIEF DESCRIPTION OF THE DRAWINGS

FIG. 2 is a perspective view of diagnostic hardware used in hand diagnosis.

FIG. 3 is a perspective view of rehabilitation hardware used with a virtual object.

FIG. 5B is an exploded view of rehabilitation hardware for the leg.

DETAILED DESCRIPTION OF THE INVENTION

During the course of this description like numbers will be used to identify like elements according to the different FIGURES which illustrate the invention.

Figure 1:
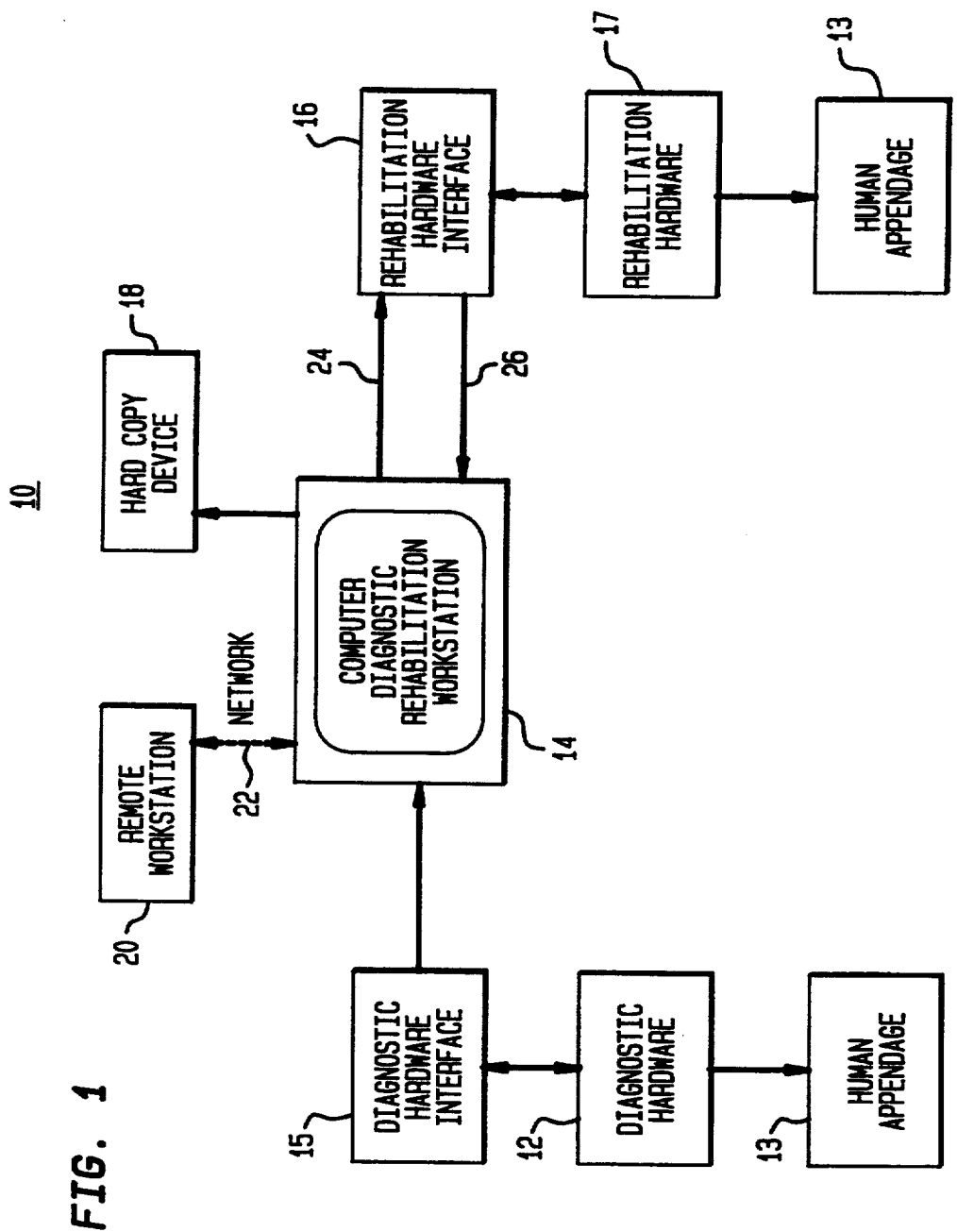
FIG. 1 is a block diagram of the computer diagnostic and rehabilitation system in accordance with the present invention.

FIG. 1 is a schematic diagram of a computerized diagnostic and rehabilitation system 10 for a human appendage in accordance with the teachings of the present invention. Human appendage 13 interacts with diagnostic hardware 12. Diagnostic hardware 12 measures the position of human appendage 13 or the force exerted by human appendage 13 against an object.

For example, diagnostic hardware 12 can be a DataGlove TM worn over the hand for sensing positions of the fingers and angles of the joints. A real object can be grasped by the user wearing the DataGlove TM and data on the force exerted by the fingers against the object can be measured. A Teletact sensing glove developed by the Advanced Robotics Research Center, U.K. and described by R. Stone in "Advanced Human System Interfaces for Telerobotics Using Virtual Reality & Telepressure Techniques" Proceedings of 1991, ICAR, Italy, 1991, can also be used for diagnostic hardware 12. Alternatively, a sensor strap can be attached to a user's arm, elbow, leg, neck or knee for providing measurements on the position of the human appendage. Force exerted by the human appendage against an object such as a bar or weight can be measured with the sensor strap. Sensors could also be incorporated into a sensor "body suit" i e in a suit which covers all or portions of the body, which can receive information on positions and force from the covered human appendage.

Diagnostic hardware 12 is connected through diagnostic hardware interface 15 to computer workstation 14. Diagnostic hardware interface 15 can be part of computer workstation 14 or a stand alone electronic box or personal computer. Computer workstation 14 analyzes data received from diagnostic hardware interface 15 for generating diagnostic information. Instructions for controlling rehabilitation can be generated from the diagnostic information in computer workstation 14. Rehabilitation hardware interface 16 controls rehabilitation hardware 17. Control signal 24 in response to the rehabilitation instructions are applied from computer workstation 14 to rehabilitation hardware interface 16. During rehabilitation, human appendage 13 contacts rehabilitation hardware 17. Response signals 26 from rehabilitation hardware 17 can be communicated to computer workstation 14. Rehabilitation hardware 17 can include an object from a "real" environment or an object from a "virtual" environment.

Workstation 14 can be coupled to hard copy device 18 for producing a hard copy of diagnostic information and rehabilitation instructions or rehabilitation progress charts. Remote workstation 20 can be coupled over network 22 to computer workstation 14. Remote workstation 20 can be used at a medical specialist location for receiving diagnostic information and communicating rehabilitation instructions to computer workstation 14.

FIG. 2 is a perspective view of diagnostic hardware 12 including a sensing glove 30 over hand 32. Sensing glove 30 provides force information when hand 32 squeezes a real object 34. Preferably, real object 34 has a spherical shape. It will be appreciated that a sensing glove such as a DataGlove TM or the glove described in U.S. Pat. No. 5,184,009 hereby incorporated by reference into this application can be used for sensing glove 30.

FIG. 3 is a perspective view of rehabilitation hardware 17 including force feedback system 40. Force feedback system 40 provides force and texture information to hand 32. Preferably, force feedback system 40 includes pneumatic cylinders 44 which provide pressure to digits 45, hand 46 and thumb 47. Virtual hand 48 and virtual object 49 are displayed on screen 50 of computer workstation 14. As the patient manipulates hand 32 and virtual hand 48 follows to attempt to grasp virtual object 49, force feedback system 40 applies appropriate pressure through pneumatic cylinders to digits 45, hand 46 and thumb 47 to simulate the compliance and tactile feel of virtual object 49. Preferably, virtual object 49 can be a sphere. Alternatively, virtual object 49 can be cylinders, squares, triangles or the like. An example of a force feedback system 40 which can be used in the present invention is described in U.S. Pat. No. 5,004,391 and U.S. Pat. No. 5,143,505 hereby incorporated by reference into this application.

Figure 4:
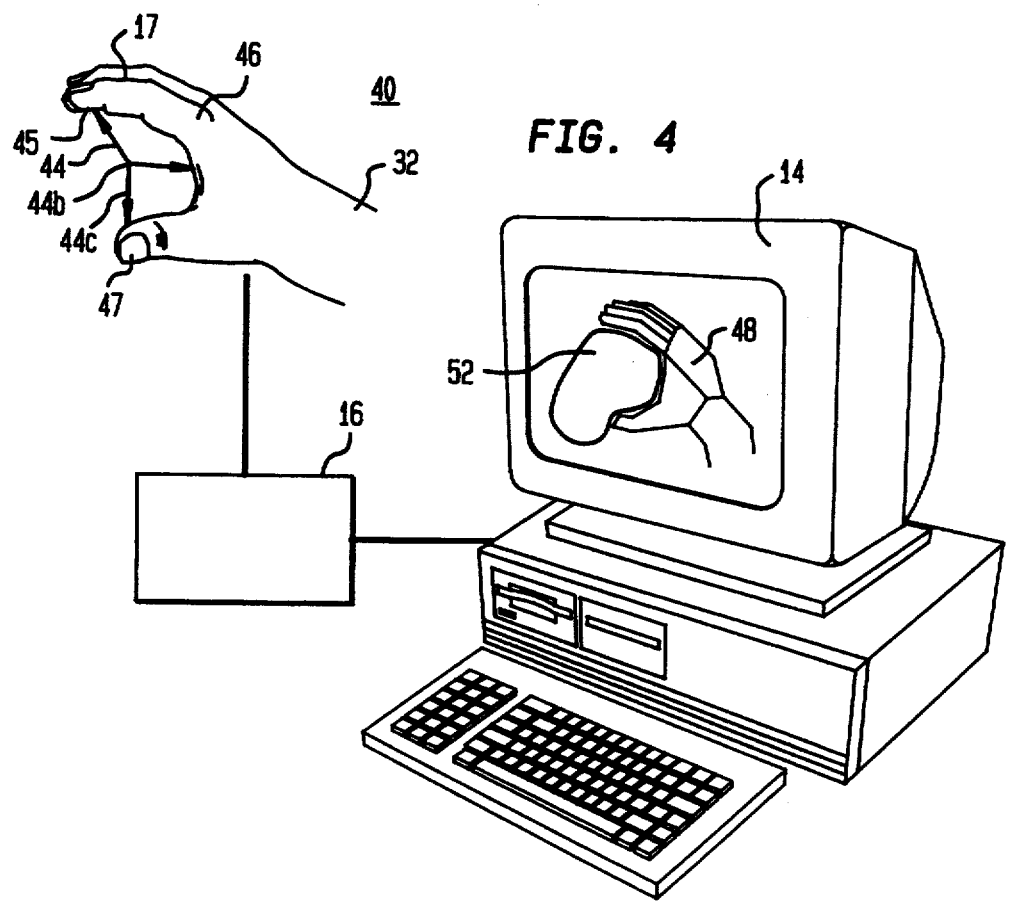
FIG. 4 is a perspective view of rehabilitation hardware for the hand used with a deformed virtual object.

FIG. 4 illustrates a perspective view of a force feedback system 40 with a deformed virtual object 52. Pneumatic cylinders 44 includes cylinders 44a attached to one or more of digits 45, cylinder 44b attached to hand 46 and cylinder 44c attached thumb 47. Deformed virtual object 52 is deformed by virtual hand 48. In response, feedback system 40 actuates pneumatic cylinder 44c to apply force to thumb 47 and on digits 45. The larger the virtual object deformation the larger the feedback force.

Figure 5A:
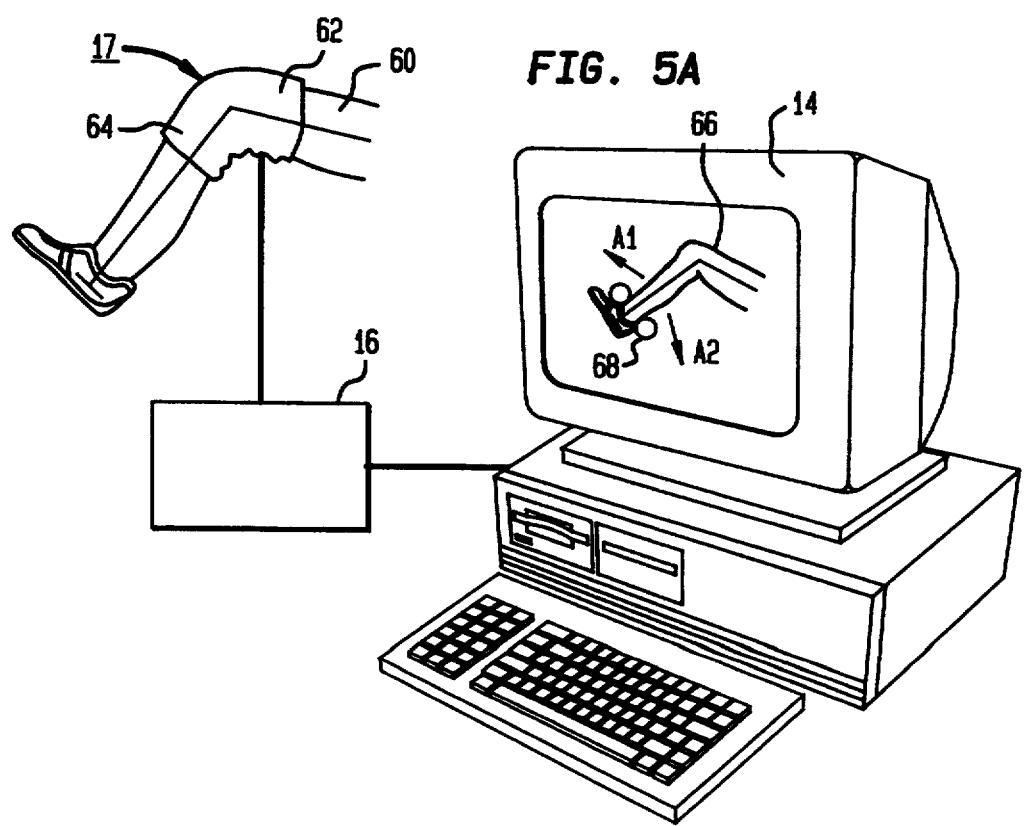
FIG. 5A is a perspective view of rehabilitation hardware for the leg used with a virtual leg exercise bar.

As shown in FIG. 5A, rehabilitation hardware 17 can be applied to a patient's leg 60. Force feedback strap 62 surrounds leg 60 and knee 64. Virtual leg 66 is displayed on workstation 14. Virtual leg 66 interacts with virtual leg exercise bar 68. Leg exercise bar 68 can move in the upward direction as illustrated by arrow $A_1$ and in the downward direction as illustrated by arrow $A_2$. Force feedback strap 62 provides feedback to leg 60 and knee 64 during movement of virtual leg 66 against leg exercise bar 68.

FIG. 5B is an exploded view of rehabilitation hardware 17 used for the leg. Upper bellow 160 is positioned on the upper portion 162 of leg 60 and lower bellow 164 is positioned on the lower portion 166 of leg 60. Support plates 168 are positioned on either side of upper bellow 160 and lower bellow 164 support plates 168 are attached to upper portion 162 and lower portion 166 of leg 60 for distributing forces from upper bellow 160 and lower bellow 164 to prevent injury to the patient. Preferably, support plates 168 are made of plastic. Pneumatic pump 172 provides air pressure to lower bellow 164 for pressurizing lower bellow 164 and releases air pressure from upper bellow 160 for depressurizing upper bellow 160. Position sensor 174 measures the position of knee joint 176. Position sensor 174, pneumatic pump 170 and pneumatic pump 172 are coupled to rehabilitation hardware interface 16.

In this embodiment, virtual leg 66 moves downward in the direction of arrow $A_2$. Upper bellow 160 is depressurized and lower bellow 164 is pressurized to simulate virtual leg 66 pressuring against virtual leg exercise bar 68.

Figure 6:
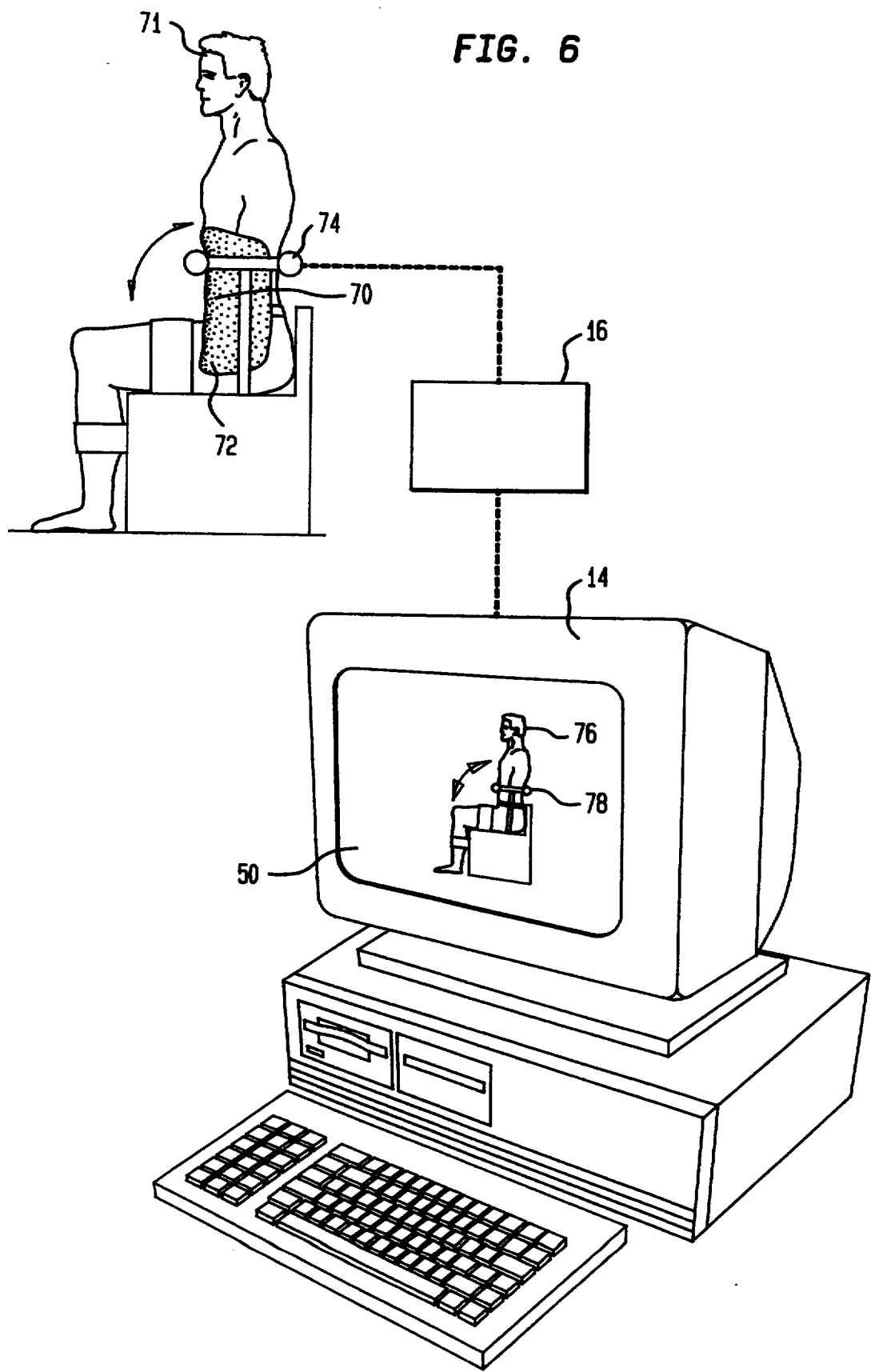
FIG. 6 is a perspective view of rehabilitation hardware for the back used with a virtual back exercise bar.

FIG. 6 is a perspective view of rehabilitation hardware 17 used for back rehabilitation. Force feedback suit 70 can be worn over the back of patient 71 and upper legs 72 for providing feedback to patient 71. Patient sits between force feedback exercise bar 74 for performing flexion and extension movements. A virtual body 76 is displayed on computer screen 50 which performs flexion and extension movements against virtual back exercise bar 78. Force feedback is provided to force feedback exercise bar 74 and feedback suit 70 in response to the movement of virtual body 76 against virtual back exercise bar 78.

Figure 7A:
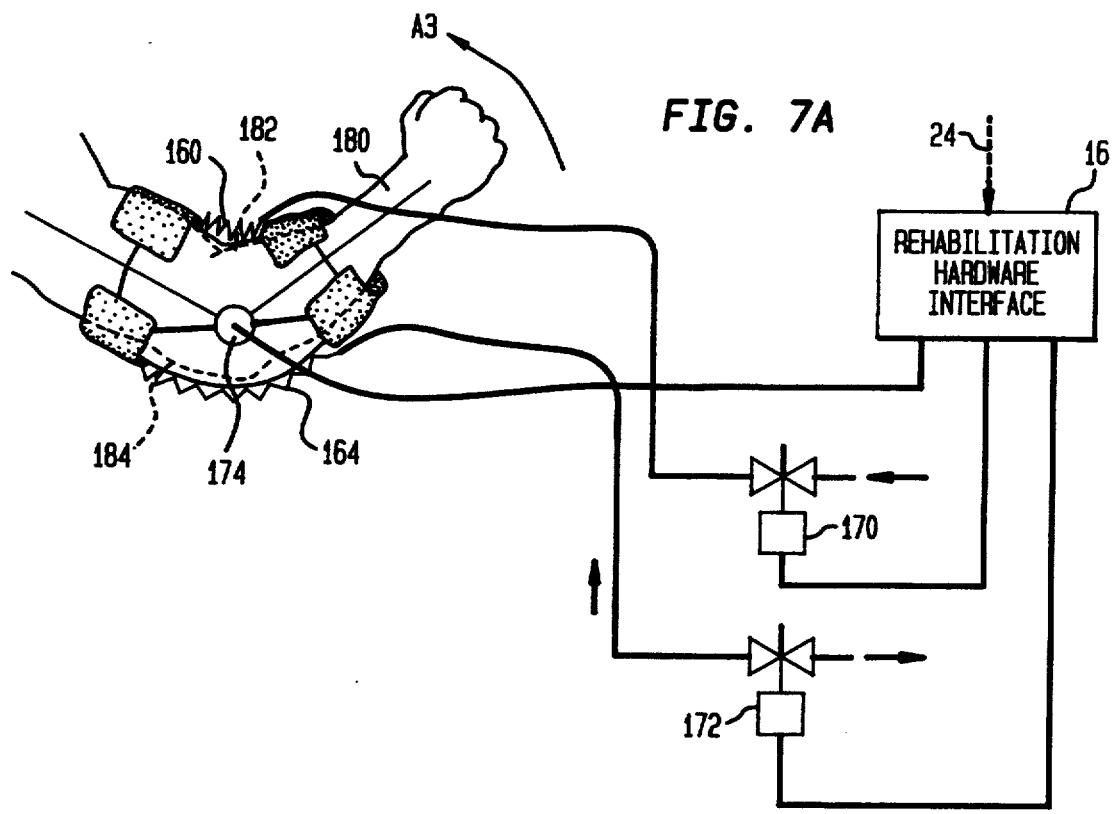
FIG. 7A is an exploded view of rehabilitation hardware for the arm.

FIG. 7A is an exploded view of rehabilitation hardware 17 used for arm 180. Upper bellow 160 is positioned on upper surface 182 of arm 180 and lower bellow 164 is positioned on lower surface 184 of arm 180. Position sensor 174 measures elbow joint angles and is sampled by rehabilitation hardware interface 16.

Figure 7B:
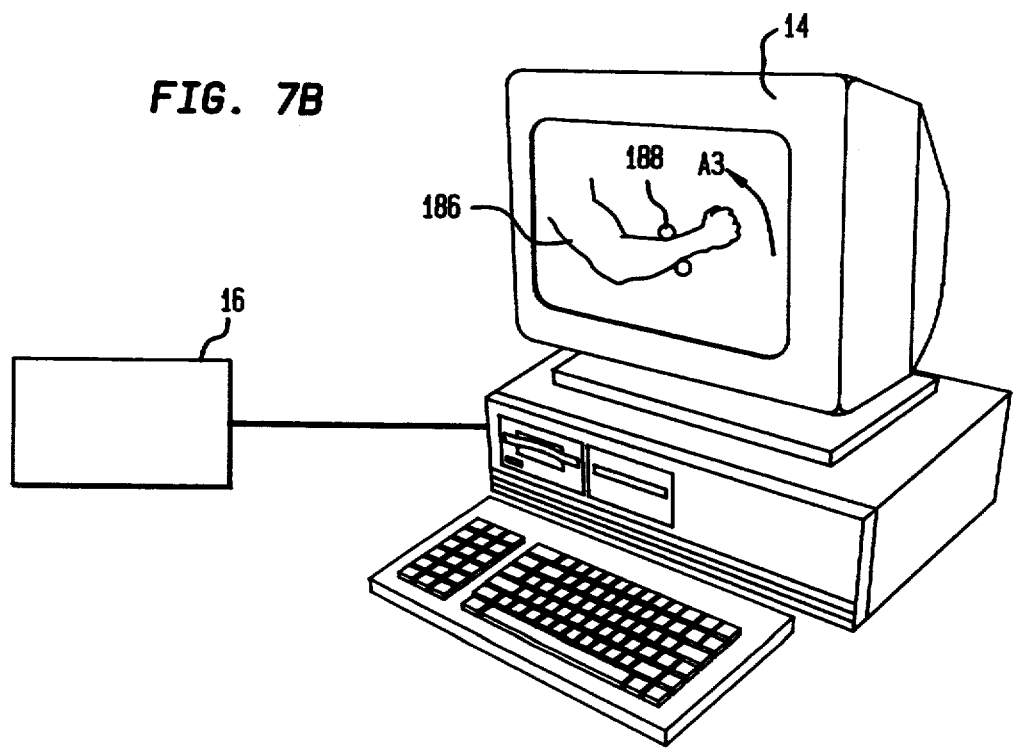
FIG. 7B is an exploded view of virtual arm and virtual arm exercise bar used with the rehabilitation hardware shown in FIG. 7A.

In this embodiment, virtual arm 186 moves upward in the direction of arrow $A_3$ against virtual arm exercise bar 188, as shown in FIG. 7B. Computer workstation 14 provides control signals 24 to rehabilitation hardware interface 16 for pressurizing upper bellow 160 and for depressurizing lower bellow 164 for simulating the application of pressure of virtual arm 186 against virtual arm exercise bar 188.

Figure 8:
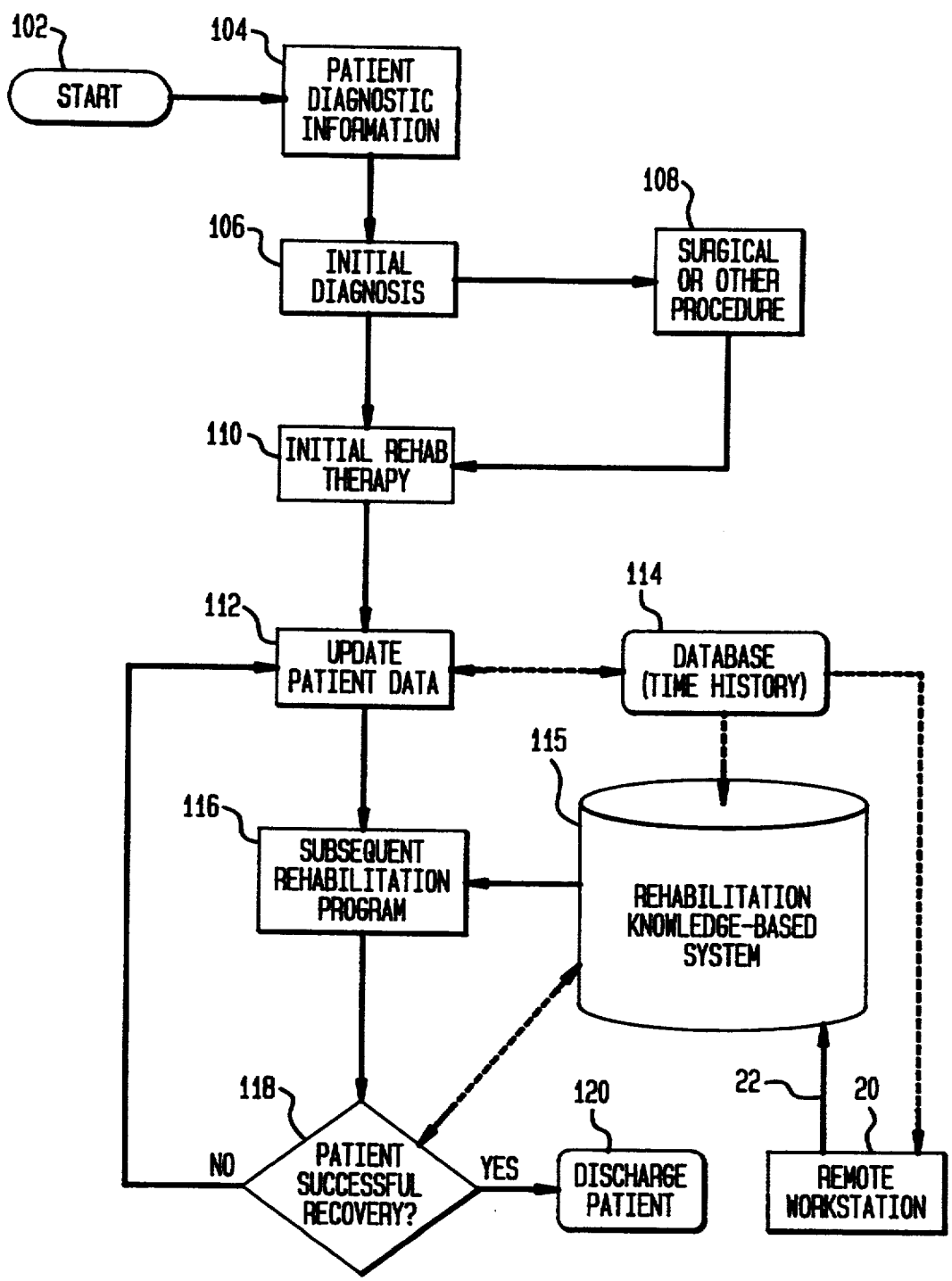
FIG. 8 is a flow diagram of an artificial intelligence program used with the computer diagnostic and rehabilitation system of the present system.

FIG. 8 is a block diagram for artificial intelligence program 100 which controls computerized diagnostic and rehabilitation system 10. Artificial intelligence program 100 is initiated in start block 102. Patient diagnostic information is received in block 104 and an initial diagnosis 106 is performed from the patient diagnosis information. For example, the initial diagnosis can be performed by comparing the patient diagnostic data with data for a human appendage without an injury.

From the initial diagnosis 106, the patient can be recommended for surgery or for another procedure in block 108. Initial rehabilitation therapy can be performed in block 110 after the initial diagnosis or after the surgical procedure. Initial rehabilitation therapy can use force feedback systems 40 or 74, force feedback strap 62 and force suit 70.

After initial rehabilitation therapy 108 is performed, patient diagnostic information from block 104 is collected and rehabilitation information is used for updating patient data in block 112. Patient data can be stored in database 114 for statistical purposes. Database 114 can include a time stamp for providing a time history of updates of the patient information. Rehabilitation knowledge based system 115 can be used to determine the condition of the human appendage by comparisons with known good human appendages or by other methods known in the art. From the rehabilitation knowledge based system 115 and from the updated patient data 112, subsequent rehabilitation therapy 116 can be recommended. In complicated cases, a specialist can be consulted through remote workstation 20 and his or her input can be transmitted to the knowledge based system 115 through network 22. Remote workstation 20 may also have access to patient database 114 through the same network 22. Measurements on successful recovery of the patient after subsequent rehabilitation therapy can be performed in block 118. If the patient has recovered, the patient will be discharged in block 120. If the patient has not recovered, the loop will return to update patient data in block 112.

The present invention has the advantage of being capable of customizing the rehabilitation regime to the progress and needs of the patient as measured by the force feedback applied to the patient. For example, the number of repetitions may be a function of the success of the patient and the nature of the virtual object may be tailored to the particular patient's needs. In addition, the system can be used for self diagnosis to minimize interaction with a therapy specialist or the system can be used with a specialist at a remote location. The same specialist can interact with a multitude of distributed rehabilitation systems which encourages access to quality health care. Finally, the system by the advantage that a time variant recovery chart can be generated by the system for monitoring the patient's progress.

While the invention has been described with reference to the preferred embodiment, this description is not intended to be limiting. It will be appreciated by those of ordinary skill in the art that modifications may be made without departing from the spirit and scope of the invention as a whole.

We claim:

1. A rehabilitation system for rehabilitating a human appendage, said system comprising:
    means for measuring position and force exerted by a human appendage,
    instruction means receiving said measurement of said position and force exerted by said human appendages and providing rehabilitation control signals; and
    force feedback rehabilitation means connected to said instruction means and attachable to said human appendages for manipulating said appendage in response to said rehabilitation control signals and feeding back to said instruction means feedback signals in response to the force exerted by said human appendages against said rehabilitation means.

2. The system of claim 1 wherein said rehabilitation means comprises a force feedback glove which is worn on said appendage.

3. The system of claim 2 wherein said force feedback glove includes:
    digit force measuring means for measuring the force exerted by at least a first digit of said hand; and,
    digit manipulation means for manipulating said first digit,
    wherein the force measured by said digit force measuring means is detected by said instruction means and employed to modify the force exerted by said digital manipulation means.

4. The system of claim 3 wherein said instruction means comprises:
    an interface means connected to said force feedback glove; and,
    a programmable computer connected to said interface means.

5. The system of claim 4 wherein said instruction means provides said rehabilitation control signals to said force feedback glove which causes said glove to simulate the reaction force of grasping a solid object.

6. The system of claim 5 wherein said force measurement means comprises;
    a sensing glove means connected to said instruction means for detecting the force exertable by said hand prior to rehabilitation.

7. The system of claim 6 wherein said instruction means includes diagnosis means for analyzing the output of said sensing glove means and producing a rehabilitation diagnosis in response thereto for implementation by said force feedback glove.

8. The system of claim 7 wherein said sensing glove means comprises said force feedback glove.

9. The system of claim 8 wherein said programmable computer includes an artificial intelligence program for performing said diagnosis means and said producing of said rehabilitation diagnosis.

10. The system of claim 9 further comprising a remote programmable computer connected to said programmable computer, said remote programmable computer including said instruction means.

11. The system of claim 10 wherein said simulated solid comprises a virtual reality simulated object.

12. The system of claim 11 wherein said virtual reality simulated object comprises a virtual sphere.

13. The system of claim 10 wherein said simulated solid object is deformable.

14. A rehabilitation method for use by a human appendage comprising the steps of:
    (a) detecting force exerted by said appendage on an object;
    (b) producing rehabilitation instructions in response to the detected force exerted by said appendage on said object;
    (c) feeding said rehabilitation instructions to a force producing means; and
    (d) exerting force with said force producing means on said appendage in response to said rehabilitation instructions.

15. The method of claim 14 further comprising the steps of:
    (e) detecting the force exerted by said appendage prior to rehabilitation to produce diagnosis information; and,
    (f) producing rehabilitation instructions in response to said diagnosis information.

16. The method of claim 15 wherein the force detected in step (a) is measured by a force feedback glove.

17. The method of claim 16 wherein said rehabilitation instructions produced in step (b) comprise instructions for said force feedback glove to simulate a virtual object.

18. The method of claim 17 wherein said virtual object comprises a sphere.

19. The method of claim 18 wherein said virtual object comprises deformable sphere.

* * * * *